(12) United States Patent  
Greiser et al.

(10) Patent No.: US 8,085,045 B2
(45) Date of Patent: Dec. 27, 2011

(54) MAGNETIC RESONANCE APPARATUS AND METHOD TO ACQUIRE AND DISPLAY CALIBRATION IMAGES

(75) Inventors: Andreas Greiser, Erlangen (DE); Sven Zuehlsdorff, Chicago, IL (US)

(73) Assignees: Siemens Aktiengesellschaft, Munich (DE); Siemens Medical Solutions USA, Inc., Malvern, PA (US)

( * ) Notice: Subject to any disclaimer, the term of this patent is extended or adjusted under 35 U.S.C. 154(b) by 208 days.

(21) Appl. No.: 12/545,174

(22) Filed: Aug. 21, 2009

(65) Prior Publication Data

US 2010/0045291 A1 Feb. 25, 2010

(30) Foreign Application Priority Data

Aug. 22, 2008 (DE) .......................... 10 2008 039 340

(51) Int. Cl.
*G01V 3/00* (2006.01)
(52) U.S. Cl. ........................................ 324/309; 324/318
(58) Field of Classification Search .......... 324/300–322; 600/407–445
See application file for complete search history.

(56) References Cited

U.S. PATENT DOCUMENTS

| | | | | |
|---|---|---|---|---|
| 7,904,139 | B2 * | 3/2011 | Chance | 600/476 |
| 2010/0056938 | A1 * | 3/2010 | Pearlman | 600/509 |
| 2010/0292568 | A1 * | 11/2010 | Droitcour et al. | 600/425 |
| 2011/0087087 | A1 * | 4/2011 | Peacock et al. | 600/410 |

OTHER PUBLICATIONS

"Artifact Reduction in True-FISP Imaging of the Coronary Arteries by Adjusting Imaging Frequency," Deshpande et al., Magnetic Resonance In Medicine, vol. 49 (2003), pp. 803-809.
"Artifacts in 3-Tesla MRI: Physical Background and Reduction Strategies," Dietrich et al., European Journal of Radiology, vol. 65 (2007), pp. 29-35.

* cited by examiner

*Primary Examiner* — Brij Shrivastav
(74) *Attorney, Agent, or Firm* — Schiff Hardin LLP

(57) ABSTRACT

In a method and magnetic resonance apparatus to acquire and present calibration images of a periodically moving organ with the use of magnetic resonance technology, calibration images are acquired by acquiring measurement data for multiple calibration images during one continuous period of the organ movement, the multiple calibration images differing in their offset frequency and/or in their spatial position in the organ to be examined, and the calibration images in a presentation manner that, from the visual quality of the respective images, allows the user to select (identify) the image acquired with the offset frequency that should then be used to acquire the diagnostic image are displayed to a user.

10 Claims, 4 Drawing Sheets

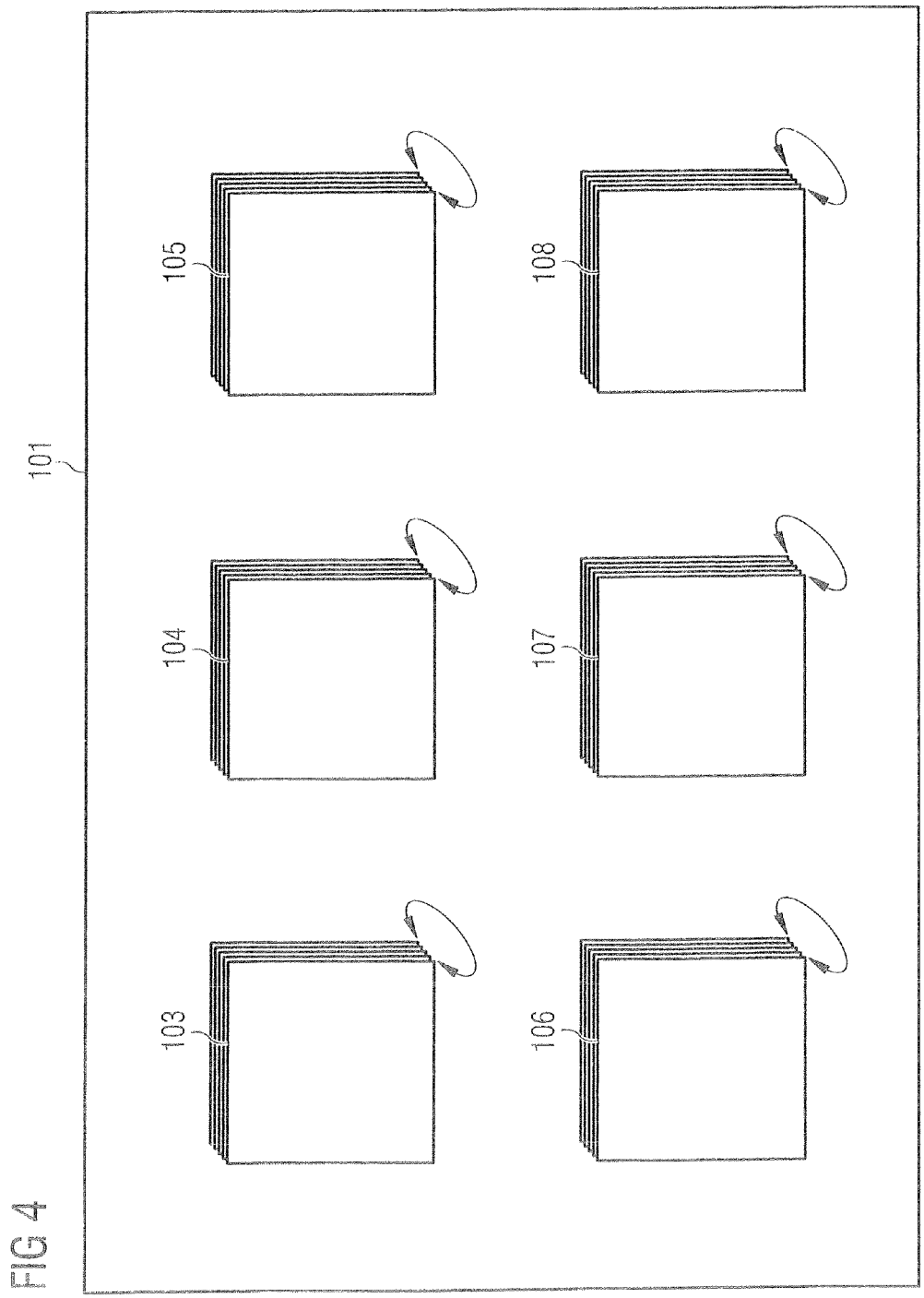

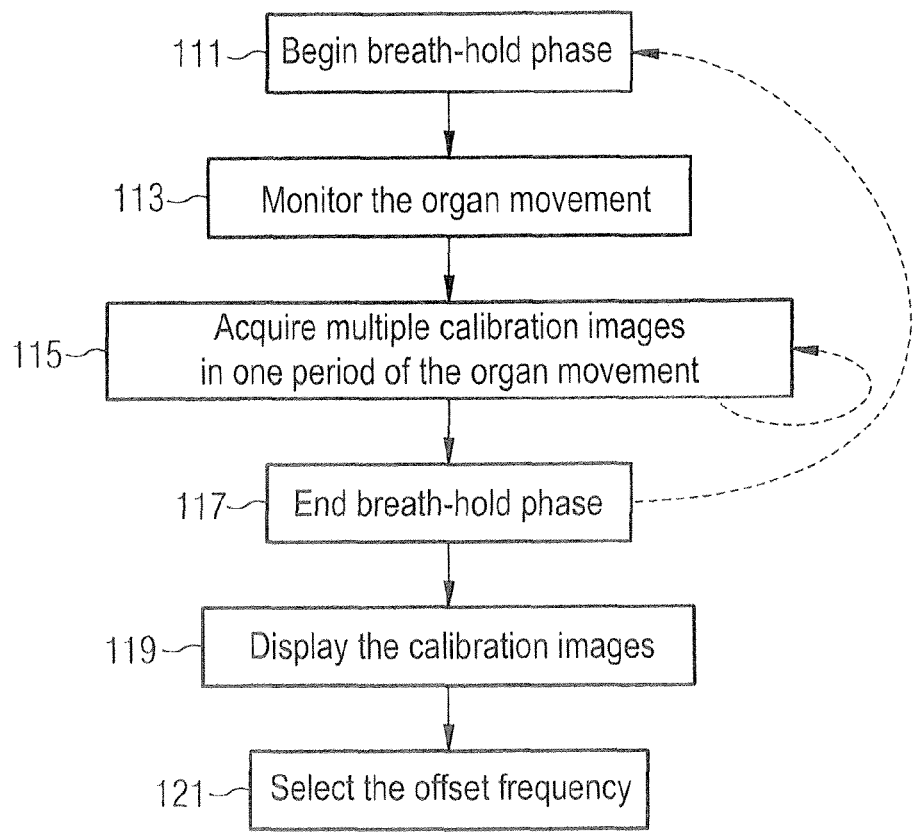

MAGNETIC RESONANCE APPARATUS AND METHOD TO ACQUIRE AND DISPLAY CALIBRATION IMAGES

BACKGROUND OF THE INVENTION

1. Field of the Invention

The present invention concerns a method to acquire and display calibration images in a periodically moving organ with the use of magnetic resonance technology. Furthermore, the invention concerns a magnetic resonance apparatus to implement such a method

2. Description of the Prior Art

Calibration images are used (among other things) in magnetic resonance imaging before diagnostically significant images of a subject to be examined are acquired and serve for the adjustment or, respectively, the optimization of the subsequent acquisition of the measurement data from which the diagnostically significant images are generated.

Magnetic resonance technology (in the following the term "magnetic resonance" is also shortened to MR) is thereby a technique that has been known for several decades with which images of the inside of an examination subject can be generated. Described in a significantly simplified way, the examination subject is positioned in a relatively strong, static, homogeneous basic magnetic field (field strengths of 0.2 Tesla to 7 Tesla or more) so that nuclear spins in the subject orient along the basic magnetic field. Radio-frequency excitation pulses are radiated into the examination subject to excite nuclear magnetic resonances, the resonant nuclear spin signal is measured, and MR images are reconstructed based thereon. For spatial coding of the measurement data, rapidly switched gradient fields are superimposed on the basic magnetic field. The acquired measurement data are digitized and stored as complex numerical values in a k-space matrix. By means of a multidimensional Fourier transformation, an associated MR image can be reconstructed from the k-space matrix populated with such values.

MR signal generation and acquisition are sensitive to small errors and inaccuracies in the technique that is used. Depending on the measurement sequence that is used, artifacts in particular increasingly occur at high field strengths of 3 Tesla or more, which are increasingly being used for diagnostic imaging.

Effects known as the off-resonance effects are one cause of image artifacts. These effects occur when the resonance frequency (Larmor frequency) of the nuclear spins to be excited differs slightly from the frequency with which the excitation pulses are radiated. For example, this slight difference can be the consequence of an insufficient shim or an insufficient frequency adjustment. In the reconstructed image, this can often appear as band-shaped artifacts, which can considerably hinder an evaluation of measured data. The TrueFISP sequence (True fast imaging with steady state precession) is one example of a known and established sequence that is sensitive to off-resonance effects.

The use of calibration images to select a suitable offset frequency is presently known in order to combat this problem. The offset frequency specifies how significantly the actual excitation frequency of an excitation pulse deviates from a previously selected excitation frequency. Such calibration images are also known as "frequency scouts". One image per heartbeat is acquired with a TrueFISP sequence over a breath-hold phase. The value for the offset frequency is varied in equal steps in a suitable frequency range across the heartbeats. The image with the best image quality can then be selected from the image series that is acquired in this way. The offset frequency associated with this image can then be used in the following TrueFISP measurement in which the diagnostic image data are then acquired with an advantageous artifact response.

FIG. 2 schematically shows the chronological workflow of this acquisition. Trigger points 47 that respectively identify the beginning of a cardiac cycle are determined between the beginning 41 and end 43 of a breath-hold phase based on the EKG signal 45. A calibration image 51 . . . 54 is respectively acquired at a defined time interval at these trigger points 47, wherein the calibration images differ in their offset frequency.

SUMMARY OF THE INVENTION

An object of the present invention is to provide a method for acquisition and display of calibration images that optimizes the discovery (identification) of the ideal offset frequency so that a subsequent acquisition of measurement data leads to images with higher quality with simultaneously faster acquisition of the calibration images. Furthermore, it is an object of the invention to provide a magnetic resonance apparatus for implementation of such a method.

In the method according to the invention for acquisition and display of calibration images in a periodically moving organ with the aid of magnetic resonance technology, calibration images are acquired in a first step in that measurement data for multiple calibration images are acquired during a continuous period of the organ movement, wherein the multiple calibration images differ in their offset frequency and/or in their spatial position in the organ to be examined, and the calibration images are displayed to a user in a second step in a presentation manner that, from the visual quality of the respective images, allows the user to select (identify) the image acquired with the offset frequency that should then be used to acquire the diagnostic image.

In contrast to known methods with which measurement data for a calibration image are acquired only in a specific phase per cardiac cycle, the method according to the invention enables the acquisition of more calibration images in the same amount of time, which distinctly increases the flexibility in the design of the method. For example, more offset frequencies can be tested, and/or calibration images from many different slices can be acquired, without distinctly increasing the measurement time. The calibration images acquired in one period differ, for instance in their spatial position and/or in their offset frequency.

As used herein "acquisition of an image" means the acquisition of magnetic resonance measurement data that are associated with this image and with which the image can be reconstructed in a further processing step.

Starting from the known method, in which one TrueFISP image was respectively acquired in the same phase of the cardiac cycle per heart beat (one TrueFISP image for each heart beat), the presentation is based on the insight that the optimal offset frequency that is determined in this manner (thus an offset frequency that initially applies only for this phase of the cardiac cycle) is applied uniformly to all cardiac phases in a subsequent measurement, and nevertheless good, satisfactory results are provided. Furthermore, it has been recognized that this situation in reverse also means that the measurement of different offset frequencies that are acquired in different phases of an organ movement still provide a sufficient information base for the optimization of the offset frequencies. This is even the case when the acquired images for selection of the offset frequency are associated with different phases of the organ movement, and therefore do not a priori necessarily need to be comparable with one another.

It has also been recognized that the phase of an organ movement has only a slight influence (if any at all) on the selection of the matching offset frequency. This allows not only a single calibration image (that is associated with a defined phase of the organ movement) but rather a plurality of calibration images to be acquired in a period of the organ movement, without the quality of the selection of the matching offset frequency being too significantly negatively affected.

Measurement data for multiple calibration images are now acquired in a period of the organ movement. This acquisition can occur in blocks, meaning that the measurement data for the different calibration images are sequentially acquired one after another.

The acquired calibration images can be two-dimensional calibration images whose spatial position in the organ to be examined is associated with a slice through the organ to be examined.

As used herein, a "periodically moving organ" means an organ exhibiting a movement pattern that repeats. The movement pattern does not have to repeat exactly over time and does not have to repeat identically. A certain range of variations typically always occurs in the movement pattern in a living subject. Organs with a periodic movement are typically the heart, the lungs, the peristalsis in the gastrointestinal tract, the pulsing of vessels, etc.

In an embodiment of the method, the calibration images for which the measurement data are acquired during a period of the organ movement differ only in terms of their offset frequency. This means that the calibration images for the different offset frequencies are acquired for the same slice during the one period. Calibration images for a different slice can then be acquired during the next period etc.

In a preferred embodiment variant, those calibration images which differ in their offset frequencies are displayed in a movie-like presentation in the display of the calibration images. For example, the calibration images that belong to one slice and to different offset frequencies can be shown sequentially one after another so that, by mere observation of the movie-like sequence, the user is able to compare images that do not belong to different offset frequencies and to determine the matching offset frequency.

In another embodiment, those calibration images that differ in their spatial position relative to the subject to be examined are displayed in parallel (next to one another) in the display of the calibration images. In particular, a combination of these two embodiment variants results in an advantageous presentation. In this case, multiple slices are presented in parallel, and the movie presentation enables a sequential consideration of the different offset frequencies. It is thus simple for a user to identify the matching offset frequency.

In the method, the periodically moving organ is advantageously the heart. Embodiments of the invention have a particularly advantageous effect in the imaging of the heart since here off-resonance effects which can often only be insufficiently combated with conventional, standard adjustment methods can occur due to a movement caused by blood flow in the circulatory system.

The method is particularly advantageous when a TrueFISP sequence which is particularly susceptible to off-resonance effects is used as the sequence for measurement data acquisition.

In the imaging of the heart it is particularly advantageous to select the spatial orientation of the calibration images is selected so that the heart is scanned in a series of short axis slices.

The magnetic resonance apparatus according to the invention has a control device that is fashioned to implement the method as described above.

BRIEF DESCRIPTION OF THE DRAWINGS

FIG. 4 shows a user-friendly presentation of the acquired calibration images.

FIG. 5 is a schematic overview of the basic steps in an embodiment of the inventive method.

DESCRIPTION OF THE PREFERRED EMBODIMENTS

Figure 1:
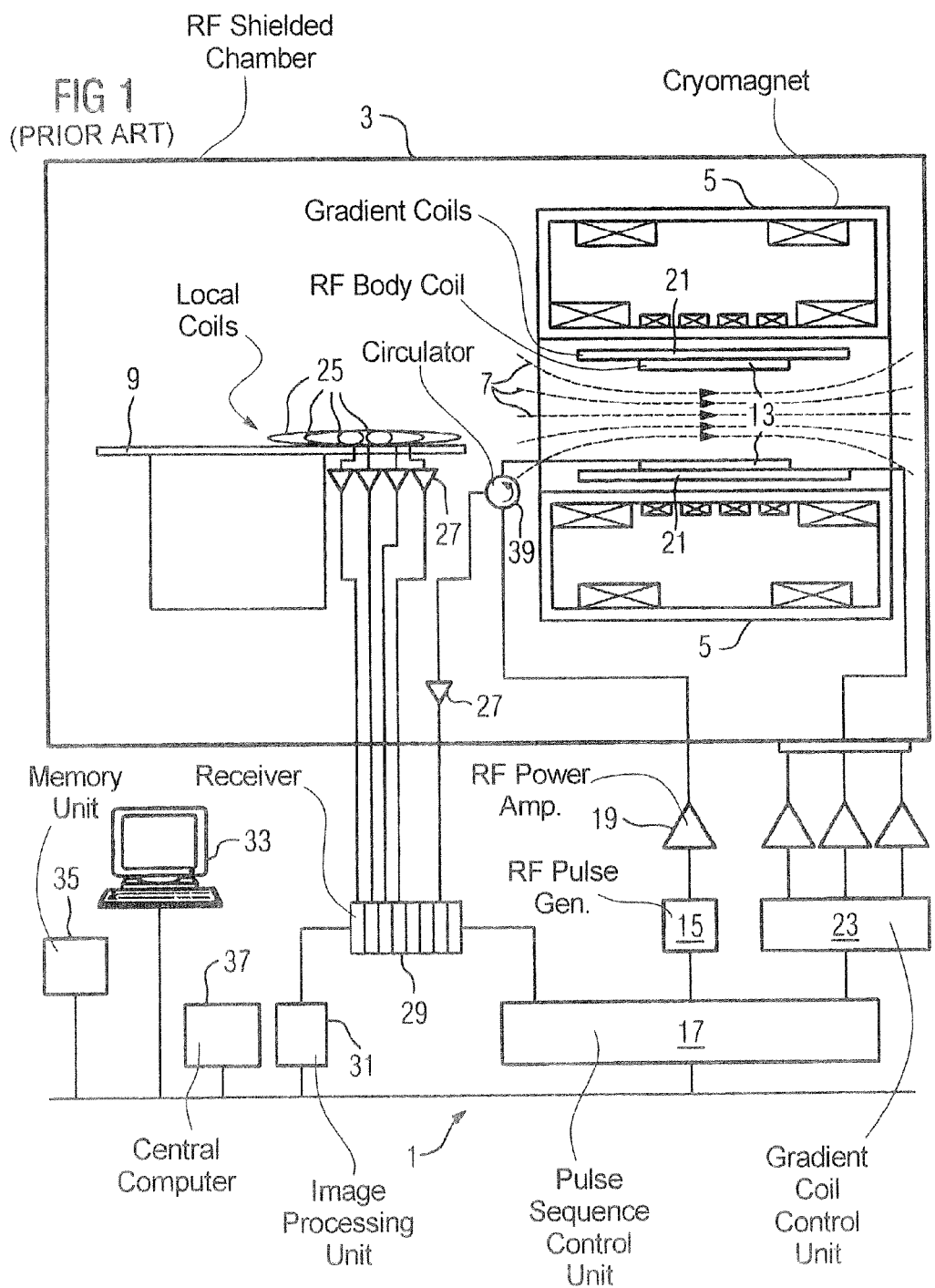
FIG. 1 schematically illustrates the basic components design of a conventional magnetic resonance apparatus.

FIG. 1 schematically shows the design of a magnetic resonance apparatus 1 with its basic components. In order to examine a body by means of magnetic resonance imaging, different magnetic fields matches to one another as precisely as possible in terms of their temporal and spatial characteristics are radiated into the body.

A strong magnet (typically a cryomagnet 5 with a tunnel-shaped opening) arranged in a measurement chamber shielded against radio frequencies generates a strong, static basic magnetic field 7 that is typically 0.2 Tesla to 3 Tesla or more. A body or a body part (not shown here) to be examined is placed on a patient bed 9 and is positioned in a homogeneous region of the basic magnetic field 7.

The excitation of the nuclear spins of the body ensues via magnetic radio-frequency excitation pulses that are radiated via a radio-frequency antenna (shown here as a body coil 13). The radio-frequency excitation pulses are generated by a pulse generation unit 15 that is controlled by a pulse sequence control unit 17. After an amplification by a radio-frequency amplifier 19, they are conducted to the radio-frequency antenna. The radio-frequency system shown here is merely schematically indicated. Typically, more than one pulse generation unit 15, more than one radio-frequency amplifier 19 and multiple radio-frequency antennas are used in a magnetic resonance apparatus 1.

Furthermore, the magnetic resonance apparatus 1 possesses gradient coils 21 with which magnetic gradient fields for selective slice excitation and for spatial coding of the measurement signal are radiated in a measurement. The gradient coils 21 are controlled by a gradient coil control unit 23 that, like the pulse generation unit 15, is connected with the pulse sequence control unit 17.

The signals emitted by the excited nuclear spins are received by the body coil 13 and/or by local coils 25, amplified by associated radio-frequency preamplifiers 27 and further processed and digitized by an acquisition unit 29.

If a coil is used that can be operated both in transmission and in reception mode, for example the body coil 13, the correct signal relaying is regulated via an upstream transmission/reception diplexer 39.

From the measurement data, an image processing unit 31 generates an image that is presented to a user via an operator console 33 or is stored in a memory unit 35. A central computer 37 controls the individual system components.

Such an MR apparatus corresponds to an MR apparatus as it is known in the prior art.

The computer 37 (and, if necessary, additional components for controlling the MR apparatus) can be configured (programmed) so that the method according to the invention can be implemented with the MR apparatus, as is subsequently explained in detail.

Figure 2:
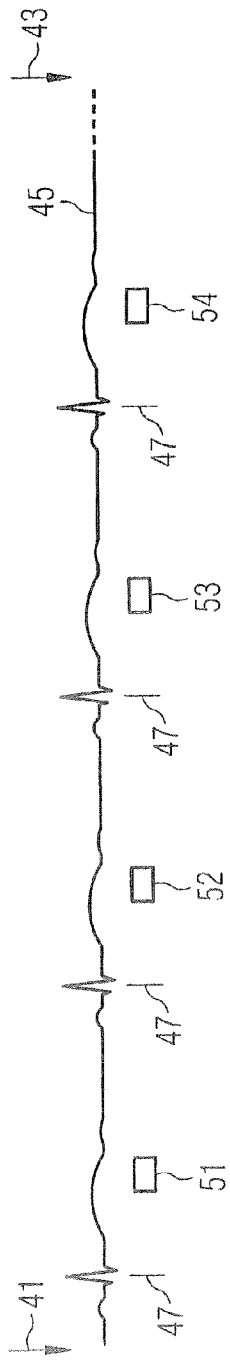
FIG. 2 illustrates a scheme for acquisition of calibration images as it is known in the prior art.

FIG. 2 shows the scheme of the chronological workflow of the acquisition of calibration images as it is known in the prior art. A detailed description of FIG. 2 has already been provided.

Figure 3:
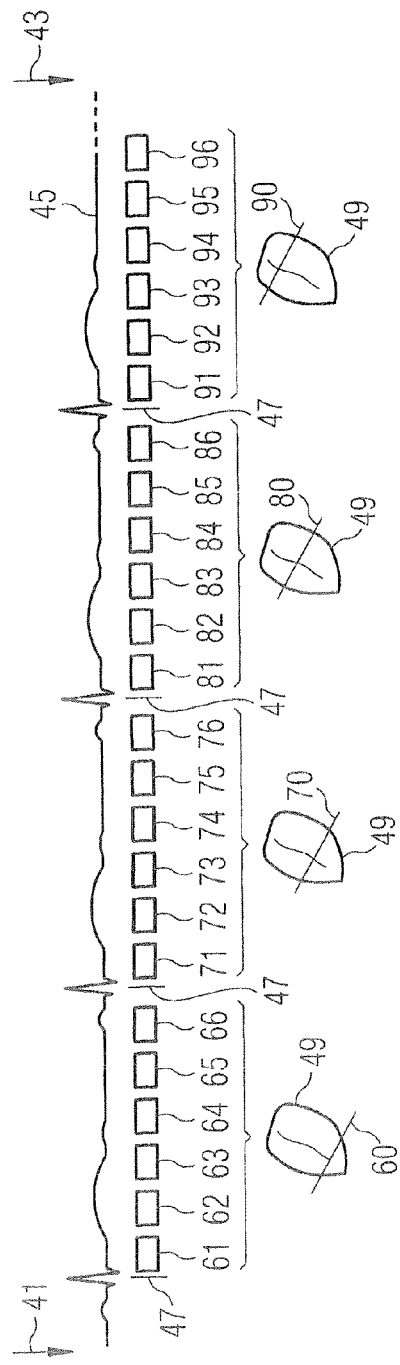
FIG. 3 illustrates a scheme for acquisition of calibration images according to one embodiment of the method.

FIG. 3 schematically shows the chronological workflow in an acquisition according to one embodiment of the invention. Here as well, trigger points 47 between the beginning 41 and end 43 of a breath-hold phase are determined based on the EKG signal 45, which trigger points 47 respectively identify the beginning of a cardiac cycle.

A plurality of calibration images 61 . . . 66, 71 . . . 76, 81 . . . 86, 91 . . . 96 is acquired in every cardiac cycle at a defined time interval relative to these trigger points 47. The acquisition of the measurement data for the calibration images 61 . . . 66, 71 . . . 76, 81 . . . 86, 91 . . . 96 thereby ensues with a single shot TrueFISP sequence.

The individual calibration images 61 . . . 66, 71 . . . 76, 81 . . . 86, 91 . . . 96 in a cardiac cycle thereby belong to a short axis slice 60, 70, 80, 90 of the heart 49. The calibration images 61 . . . 66, 71 . . . 76, 81 . . . 86, 91 . . . 96 of a cardiac cycle differ in their offset frequency.

In a first cardiac cycle, the first calibration image 61 is acquired with, for example, a first offset frequency v1, the second calibration image 62 is acquired with a second offset frequency v2 etc. The offset frequencies v1, v2 . . . vn can thereby be gradually increased from calibration image to calibration image so that the frequency range of interest for the short axis slice 60 is already covered in a few cardiac cycles.

In a second cardiac cycle, the first calibration image 71 is in turn acquired with the first offset frequency v1, the second calibration image 72 is acquired with the second offset frequency v2 etc.

A different offset frequency is thus associated with every time phase of the cardiac cycle.

A number of calibration images 61 . . . 66, 71 . . . 76, 81 . . . 86, 91 . . . 96 that belong both to different offset frequencies and to different short axis slices 60, 70, 80, 90 of the heart can be acquired in a single breath-hold phase in this way. It is even possible that all slice geometries (which typically must be covered for a left ventricular function analysis, for example)—i.e. 8 to 12 short axis slices—are measured in a single breath-hold phase and subsequently are optimized with regard to the offset frequency.

The sorting of the calibration images with regard to the cardiac cycles that is described using FIG. 3 is one advantageous possibility for the sorting of the calibration images. Other possibilities are also conceivable, for example in that calibration images with different spatial positions that, however, belong to a single offset frequency are acquired in one cardiac cycle, and calibration images with the same different spatial positions that then belong to a different offset frequency are acquired in a next cardiac cycle etc. A combination of the sorting just described and the sorting described using FIG. 3 is also possible.

The calibration images are presented to a user after all of the calibration images 61 . . . 66, 71 . . . 76, 81 . . . 86, 91 . . . 96 have been acquired.

An advantageous presentation of the calibration images is explained using FIG. 4.

The calibration images 61 . . . 66, 71 . . . 76, 81 . . . 86, 91 . . . 96 are thereby displayed in parallel in groups 103 . . . 108 on a display device 101. The calibration images of different offset frequency that belong to one of the short axis slices 60, 70, 80, 90 of the heart 49 are thereby respectively combined into one group 103 . . . 108. For presentation of the different offset frequencies, the calibration images are thereby displayed in a movie-like presentation, wherein the individual offset frequencies are shown in chronological order in the manner of a movie (indicated by the arrows in the drawing). This way a user can quickly get an overview of the quality of the individual calibration images per slice and for different offset frequencies. The user can thereby affect the movie-like presentation in that, for example, he can scroll forward and back, can pause the movie-like presentation, etc.

This allows a user to also quickly assess the calibration images 61 . . . 66, 71 . . . 76, 81 . . . 86, 91 . . . 96 with regard to stripe artifacts for different slice orientations and to select the matching offset frequency for a subsequent acquisition. The user thus can determine the matching offset frequency separately for every slice 60, 70, 80, 90; however, it is also possible to determine a common offset frequency that represents a compromise for the stripe artifacts with regard to all slices.

FIG. 5 schematically shows individual method steps of an embodiment of the method.

After beginning of a breath-hold phase (Step 111), the periodic organ movement of the organ to be examined is monitored (Step 113). The acquisition of multiple calibration images (Step 115) ensues in one period of the organ movement. This calibration images differ with regard to their spatial position in the organ to be examined and/or with regard to their offset frequency. The acquisition of the calibration images is respectively continued in the following periods of the organ movement until the end of the breath-hold phase (Step 117) is reached. In the event that it is necessary, the reintroduction of a breath-hold phase and an additional acquisition of calibration images ensue. After all desired calibration images have been acquired, the calibration images are shown to a user (Step 119). This presentation allows the user to select the matching offset frequency for the subsequent acquisition of the diagnostically relevant images (Step 121).

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to acquire and present calibration images of a periodically moving organ using magnetic resonance technology, comprising the steps of:
   exposing an examination subject, containing a periodically moving organ, to acquire a plurality of calibration images during one continuous period of said organ movement, said multiple calibration images differing as to at least one of offset frequency and spatial position relative to the organ; and
   displaying said calibration images at a display in a presentation manner that, from the visual quality of the respective, displayed images, allows the user to select an image acquired with an offset frequency that should then be used to acquire a diagnostic image of the periodically moving organ.

2. A method as claimed in claim 1 comprising acquiring calibration images during said one period of the organ movement that differ only as to said offset frequency.

3. A method as claimed in claim 1 comprising acquiring said calibration images during a breath-hold comprising multiple periods of the organ movement.

4. A method as claimed in claim 1 comprising acquiring said calibration images so as to differ as to offset frequency, and displaying said calibration images in a movie presentation at a display.

5. A method as claimed in claim 1 comprising acquiring calibration images that differ as to spatial position, and displaying said calibration images next to one another at a display.

6. A method as claimed in claim 1 comprising acquiring said calibration images of the heart of the subject, as said periodically moving organ.

7. A method as claimed in claim 6 comprising acquiring said calibration images as a series of short axis slices of the heart.

8. A method as claimed in claim 1 comprising employing a TrueFISP sequence as said magnetic resonance data acquisition sequence.

9. A magnetic resonance apparatus comprising:

a magnetic resonance data acquisition unit configured to receive an examination subject therein, said examination subject containing a periodically moving organ;

a control unit configured to operate said magnetic resonance data acquisition unit to acquire a plurality of calibration images of the organ during one period of movement of the organ, said plurality of calibration images differing as to at least one of offset frequency and spatial position of the organ; and said control unit being configured to display said plurality of calibration images at a display connected to the control unit, in a presentation manner that, from a visual quality of the respective, displayed images, allows a user to select an image acquired with an offset frequency that should be used to acquire a diagnostic image of the organ.

10. A magnetic resonance apparatus as claimed in claim 9 wherein said control unit is configured to operate said magnetic resonance data acquisition unit with a TrueFISP sequence to acquire said calibration images.

\* \* \* \* \*